US006671626B2

(12) United States Patent
Silverman

(10) Patent No.: US 6,671,626 B2
(45) Date of Patent: Dec. 30, 2003

(54) DETERMINATION AND USE OF THREE-DIMENSIONAL MOMENTS OF MOLECULAR PROPERTY FIELDS

(75) Inventor: Benjamin D. Silverman, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/766,741

(22) Filed: Jan. 22, 2001

(65) Prior Publication Data

US 2002/0133298 A1 Sep. 19, 2002

Related U.S. Application Data

(60) Provisional application No. 60/238,698, filed on Oct. 6, 2000.

(51) Int. Cl.[7] ................................. G01N 31/00
(52) U.S. Cl. .................. 702/27; 702/150; 702/152; 702/22; 702/23; 702/153
(58) Field of Search .................. 702/19, 150, 27, 702/23, 152, 153

(56) References Cited

U.S. PATENT DOCUMENTS 5,784,294 A * 7/1998 Platt et al. ................... 702/27

OTHER PUBLICATIONS

Todeschini, R. and Gramatica, P., "New 3D Molecular Descriptors: The Whim Theory and QSAR Applications", 3D QSAR in Drug Design, Kluwer Academic Publishers, vol. 2, Part 3, p. 355–380 (1998).

Ganica, E., Bravi, G., Mascagni, P., and Zaliani, A., "Global 3D–QSAR Methods: MS–WHIM and Autocorrelation", Kluwer Academic Publishers, Journal of Computer–Aided Molecular Design, 14, p. 293–306 (2000).

* cited by examiner

Primary Examiner—Marianne P. Allen
Assistant Examiner—Lori A. Clow
(74) Attorney, Agent, or Firm—Ryan, Mason & Lewis, LLP; Casey P. August, Esq.

(57) ABSTRACT

Generally, the present invention provides and uses a set of descriptors of three-dimensional molecular property fields. A portion of the descriptors are calculated in such a way as to separate property fields from the underlying structure of the molecule. These descriptors are calculated through reference to a property field center. Thus, only if the property field changes, such as by moving an atom having a non-zero property value, will the descriptors need to be recalculated. Additionally, a portion of the descriptors do relate to the underlying molecular structure, only these descriptors contain information from more than one reference point. In particular, a displacement is determined between a property field center and the centroid of a molecule. This descriptor contains information from two reference points. Furthermore, components of a property field are mapped onto a principal geometric frame, which essentially references the property field to the molecular shape. These descriptors thus contain information relating to the geometric frame of the molecule.

37 Claims, 9 Drawing Sheets

| Molecule | pEC$_{50}$ | Molecule | pEC$_{50}$ |
|---|---|---|---|
| 1-Cl | 4.000 | 2-Br | 6.530 |
| 1,2,3,4-Cl$_4$ | 5.866 | 2,3,6-Cl$_3$ | 6.658 |
| 1,2,3,4,6,7,8,9-Cl$_8$ | 5.000 | 2,3,6,7-Cl$_4$ | 6.796 |
| 1,2,3,4,7-Cl$_5$ | 5.194 | 2,3,7-Br$_3$ | 8.932 |
| 1,2,3,4,7,8-Cl$_6$ | 6.553 | 2,3,7-Cl$_3$ | 7.149 |
| 1,2,3,7,8-Br$_5$ | 8.180 | 2,3,7,8-Br$_4$ | 8.824 |
| 1,2,3,7,8-Cl$_5$ | 7.102 | 2,3,7,8-Cl$_4$ | 8.000 |
| 1,2,4-Cl$_3$ | 4.886 | 2,7-Br$_2$ | 7.810 |
| 1,2,4,7,8-Br$_5$ | 7.770 | 2,8-Cl$_2$ | 5.495 |
| 1,2,4,7,8-Cl$_5$ | 5.959 | 3,7-Cl$_2$-2,8-Br$_2$ | 9.350 |
| 1,3,7,8-Br$_4$ | 8.699 | 3,7,8-Cl$_3$-2-Br$_2$ | 7.939 |
| 1,3,7,8-Cl$_4$ | 6.102 | 7,8-Cl$_2$-2,3-Br$_2$ | 8.830 |
| 1,3,7,8,9-Br$_5$ | 7.030 | | |

| Molecule | pEC$_{50}$ | Molecule | pEC$_{50}$ |
| --- | --- | --- | --- |
| 1,2,3,4,7,8 | 6.638 | 2,3 | 5.326 |
| 1,2,3,4,8 | 6.921 | 2,3,4 | 4.721 |
| 1,2,3,6 | 6.456 | 2,3,4,6 | 6.456 |
| 1,2,3,6,7,8 | 6.569 | 2,3,4,6,7,8 | 7.328 |
| 1,2,3,7 | 6.959 | 2,3,4,7 | 7.602 |
| 1,2,3,7,8 | 7.128 | 2,3,4,7,8 | 7.824 |
| 1,2,3,7,9 | 6.398 | 2,3,4,7,9 | 6.699 |
| 1,2,4,6,7 | 7.169 | 2,3,4,8 | 6.699 |
| 1,2,4,6,7,8 | 5.081 | 2,3,6,8 | 6.658 |
| 1,2,4,6,8 | 5.509 | 2,3,7,8 | 7.387 |
| 1,2,4,7,8 | 5.886 | 2,3,8 | 6.000 |
| 1,2,4,7,9 | 4.699 | 2,6 | 3.609 |
| 1,2,4,8 | 5.000 | 2,6,7 | 6.347 |
| 1,3,4,7,8 | 6.699 | 2,8 | 3.590 |
| 1,3,6 | 5.357 | 3 | 4.377 |
| 1,3,6,8 | 6.658 | 4 | 3.000 |
| 1,3,8 | 4.071 | No Substituent | 3.000 |
| 2 | 3.553 | | |

FIG. 5

| Molecule | pEC$_{50}$ | Molecule | pEC$_{50}$ |
|---|---|---|---|
| 2,2',4,4' | 3.886 | 2,3',4,4',5 | 5.041 |
| 2,2',4,4',5,5' | 4.102 | 2,3',4,4',5,5' | 4.796 |
| 2,3,3',4,4' | 5.367 | 2,3',4,4',5',6 | 4.004 |
| 2,3,3',4,4',5 | 5.301 | 2',3,4,4',5 | 4.854 |
| 2,3,3',4,4',5' | 5.149 | 3,3',4,4' | 6.149 |
| 2,3,4,4',5 | 5.387 | 3,3',4,4',5 | 6.886 |
| 2,3,4,5 | 3.854 | 3,4,4',5 | 4.553 |

| Molecule | $I_x^g$ | $I_y^g$ | $I_z^g$ | $m_0$ | $|d|$ | $Q_{xx}^c$ | $Q_{yy}^c$ | $Q_{zz}^c$ | $\Theta_1$ | $\Theta_2$ | $\Theta_3$ |
|---|---|---|---|---|---|---|---|---|---|---|---|
| 1 | 50.14 | 187.68 | 237.82 | 3.36 | 0.76 | 19.55 | 38.35 | 57.90 | 5.18 | 11.50 | 16.67 |
| 2 | 55.80 | 198.78 | 254.58 | 5.14 | 1.81 | 31.46 | 77.83 | 109.29 | 6.12 | 11.85 | 17.97 |
| 3 | 65.17 | 210.01 | 275.18 | 7.52 | 0.00 | 50.87 | 122.87 | 173.74 | 6.76 | 16.34 | 23.10 |
| 4 | 56.70 | 204.45 | 261.15 | 5.74 | 1.07 | 33.19 | 97.26 | 130.45 | 5.63 | 15.96 | 21.59 |
| 5 | 57.69 | 210.01 | 267.69 | 6.33 | 0.45 | 35.36 | 115.96 | 151.32 | 5.59 | 18.11 | 23.70 |
| 6 | 55.17 | 213.61 | 268.79 | 7.21 | 0.52 | 34.75 | 150.20 | 184.94 | 4.61 | 20.78 | 25.39 |
| 7 | 53.92 | 209.97 | 263.89 | 5.74 | 0.44 | 27.38 | 112.58 | 139.95 | 4.62 | 19.60 | 24.21 |
| 8 | 54.82 | 193.28 | 248.09 | 4.55 | 1.36 | 29.28 | 60.12 | 89.40 | 6.24 | 11.57 | 17.81 |
| 9 | 58.44 | 207.15 | 265.59 | 7.21 | 0.22 | 43.39 | 127.95 | 171.33 | 5.88 | 17.84 | 23.72 |
| 10 | 56.70 | 204.45 | 261.15 | 5.74 | 0.19 | 33.19 | 97.55 | 130.75 | 5.69 | 17.08 | 22.76 |
| 11 | 54.11 | 207.10 | 261.20 | 6.32 | 0.48 | 32.18 | 122.35 | 154.52 | 5.04 | 19.18 | 24.22 |
| 12 | 52.99 | 204.41 | 257.40 | 5.14 | 0.40 | 25.62 | 93.85 | 119.46 | 4.94 | 18.13 | 23.08 |
| 13 | 58.39 | 207.14 | 265.53 | 7.27 | 0.93 | 43.07 | 128.02 | 171.08 | 5.51 | 17.16 | 22.67 |
| 14 | 47.47 | 194.18 | 241.65 | 3.65 | 1.41 | 14.57 | 62.32 | 76.89 | 3.60 | 15.49 | 19.09 |
| 15 | 52.02 | 198.80 | 250.81 | 4.55 | 1.20 | 23.45 | 74.95 | 98.40 | 4.69 | 15.52 | 20.20 |
| 16 | 52.85 | 204.52 | 257.36 | 5.14 | 0.70 | 24.79 | 94.41 | 119.20 | 4.13 | 18.57 | 22.70 |
| 17 | 49.68 | 207.14 | 256.82 | 5.43 | 0.93 | 20.38 | 117.34 | 137.72 | 3.51 | 20.99 | 24.50 |
| 18 | 49.21 | 204.44 | 253.66 | 4.55 | 0.75 | 17.69 | 90.49 | 108.18 | 3.73 | 19.51 | 23.24 |
| 19 | 50.84 | 213.59 | 264.43 | 6.32 | 0.01 | 23.62 | 144.87 | 168.49 | 3.74 | 22.93 | 26.66 |
| 20 | 50.22 | 209.96 | 260.17 | 5.14 | 0.01 | 19.85 | 109.04 | 128.89 | 3.86 | 21.21 | 25.07 |
| 21 | 48.43 | 200.84 | 249.26 | 4.54 | 0.01 | 16.60 | 91.05 | 107.66 | 3.00 | 20.72 | 23.72 |
| 22 | 48.30 | 198.83 | 247.13 | 3.95 | 0.53 | 15.82 | 71.91 | 87.73 | 3.72 | 18.21 | 21.92 |
| 23 | 50.52 | 211.80 | 262.32 | 5.73 | 0.18 | 21.72 | 126.96 | 148.69 | 3.76 | 22.16 | 25.92 |
| 24 | 50.36 | 210.90 | 261.26 | 5.44 | 0.31 | 20.77 | 118.01 | 138.78 | 3.80 | 21.64 | 25.44 |
| 25 | 50.52 | 211.80 | 262.31 | 5.73 | 0.56 | 21.73 | 126.91 | 148.64 | 3.79 | 21.84 | 25.63 |

FIG. 7

| | $I_x^g$ | $I_y^g$ | $I_z^g$ | $m_0$ | $|d|$ | $Q_{xx}^c$ | $Q_{yy}^c$ | $Q_{zz}^c$ | $\Theta_1$ | $\Theta_2$ | $\Theta_3$ |
|---|---|---|---|---|---|---|---|---|---|---|---|
| $I_x^g$ | 1 | 0.433 | 0.422 | 0.824 | -0.176 | 0.948 | 0.538 | 0.651 | 0.672 | 0.049 | 0.153 |
| $I_y^g$ | 0.433 | 1 | 0.938 | 0.442 | -0.129 | 0.255 | 0.78 | 0.727 | -0.046 | 0.77 | 0.75 |
| $I_z^g$ | 0.422 | 0.938 | 1 | 0.375 | -0.124 | 0.313 | 0.741 | 0.757 | 0.111 | 0.763 | 0.853 |
| $m_0$ | 0.824 | 0.442 | 0.375 | 1 | -0.338 | 0.828 | 0.796 | 0.833 | 0.288 | 0.332 | 0.323 |
| $|d|$ | -0.176 | -0.129 | -0.124 | -0.338 | 1 | -0.21 | -0.336 | -0.332 | 0.023 | -0.377 | -0.359 |
| $Q_{xx}^c$ | 0.948 | 0.255 | 0.313 | 0.828 | -0.21 | 1 | 0.488 | 0.645 | 0.746 | -0.024 | 0.132 |
| $Q_{yy}^c$ | 0.538 | 0.78 | 0.741 | 0.796 | -0.336 | 0.488 | 1 | 0.969 | -0.05 | 0.812 | 0.783 |
| $Q_{zz}^c$ | 0.651 | 0.727 | 0.757 | 0.833 | -0.332 | 0.645 | 0.969 | 1 | 0.162 | 0.722 | 0.774 |
| $\Theta_1$ | 0.672 | -0.046 | 0.111 | 0.288 | 0.023 | 0.746 | -0.05 | 0.162 | 1 | -0.425 | -0.143 |
| $\Theta_2$ | 0.049 | 0.77 | 0.763 | 0.332 | -0.377 | -0.024 | 0.812 | 0.722 | -0.425 | 1 | 0.937 |
| $\Theta_3$ | 0.153 | 0.75 | 0.853 | 0.323 | -0.359 | 0.132 | 0.783 | 0.774 | -0.143 | 0.937 | 1 |

FIG. 8

|  | 1 | 2 | 3 | 4 | 5 | 6 | 7 | 8 | 9 | 10 | 11 |
|---|---|---|---|---|---|---|---|---|---|---|---|
| $I_x^g$ | 0.272 | -0.419 | 0.062 | -0.039 | 0.34 | -0.468 | 0.567 | -0.133 | 0.262 | -0.043 | 0.003 |
| $I_y^g$ | 0.338 | 0.171 | 0.319 | 0.051 | 0.61 | 0.287 | -0.025 | 0.166 | -0.349 | -0.385 | -0.022 |
| $I_z^g$ | 0.342 | 0.149 | 0.376 | 0.301 | 0.136 | -0.121 | -0.463 | -0.203 | 0.414 | 0.411 | 0.026 |
| $m_0$ | 0.317 | -0.259 | -0.24 | -0.444 | 0.029 | 0.21 | -0.26 | 0.54 | 0.416 | -0.019 | -0.001 |
| $|d|$ | -0.153 | -0.033 | 0.793 | -0.493 | -0.281 | -0.074 | 0.072 | 0.116 | -0.02 | 0.005 | -0.002 |
| $Q_{xx}^c$ | 0.249 | -0.463 | -0.037 | -0.003 | -0.125 | -0.386 | -0.411 | 0.038 | -0.601 | 0.077 | 0.141 |
| $Q_{yy}^c$ | 0.386 | 0.076 | -0.081 | -0.291 | -0.113 | 0.387 | 0.25 | -0.363 | -0.147 | 0.306 | 0.531 |
| $Q_{zz}^c$ | 0.394 | -0.024 | -0.043 | -0.147 | -0.321 | 0.106 | -0.073 | -0.471 | 0.02 | -0.332 | -0.607 |
| $\Theta_1$ | 0.068 | -0.501 | 0.224 | 0.53 | -0.261 | 0.483 | 0.222 | 0.195 | -0.005 | 0.12 | -0.101 |
| $\Theta_2$ | 0.306 | 0.383 | -0.076 | -0.002 | -0.104 | -0.175 | 0.31 | 0.399 | -0.249 | 0.482 | -0.404 |
| $\Theta_3$ | 0.325 | 0.292 | 0.031 | 0.281 | -0.451 | -0.247 | 0.096 | 0.236 | 0.14 | -0.475 | 0.393 |
| variances | 6.1124 | 2.8087 | 1.0688 | 0.6498 | 0.2858 | 0.0417 | 0.0202 | 0.0082 | 0.0041 | 0.0003 | 0.0001 |

DETERMINATION AND USE OF THREE-DIMENSIONAL MOMENTS OF MOLECULAR PROPERTY FIELDS

CROSS REFERENCE TO RELATED APPLICATIONS

This application claims the benefit of U.S. Provisional Application No. 60/238,698, filed Oct. 6, 2000.

FIELD OF THE INVENTION

The present invention relates to mathematical descriptors of molecules and, more particularly, relates to the determination and use of three-dimensional moments of molecular property fields.

BACKGROUND OF THE INVENTION

The three-dimensional characterization of molecular physical and chemical properties has been a subject of interest because of numerous procedures that attempt to correlate this characterization with molecular biological activity. The expectation is that three-dimensional molecular features should be central to the delivery and binding of a drug molecule to its targeted receptor site. Molecules with similar three-dimensional features should interact the same. Thus, if there is a first drug molecule that binds well with a targeted receptor site and a second drug molecule that has particular three-dimensional features similar to features of the first drug molecule, it is expected that the second drug molecule will also bind well with this targeted receptor site.

There are a variety of three-dimensional molecular analysis procedures that are in use and that attempt to compare two molecules for molecular similarities. Molecular analysis procedures that involve descriptions of molecular properties, which in turn can relate to the biological activity of the molecules, are often called Quantitative Structure Activity Relations (QSAR).

Some of these three-dimensional molecular analysis procedures involve the detailed enumeration of molecular properties over a set of grid points. To be able to properly compare two molecules, these procedures subsequently require an alignment or superposition step. This step attempts to align two molecules so that features of the molecules may be compared. This alignment step is required if there is a detailed characterization of a three-dimensional molecular property field, whether the property field is steric, electrostatic, or hydrophobic.

One problem with these procedures, or any procedure that requires an alignment, is that the alignment may not be correct. This can lead to an incorrect analysis. Additionally, it is very hard to determine, for complex structures, where and how to align two structures. Finally, alignment can be time consuming and numerically intensive. This is particularly true because three-dimensional rotations and translations must be performed in order to align two molecules. These translations and rotations take processing power and time. Moreover, after each translation or rotation, the similarities between the two molecules must be determined again.

Another procedure for comparing two molecules is to create a similarity matrix. While similarity matrices significantly reduce the number of descriptors compared with the grid based procedures, they still require a molecular alignment step.

There have, however, been a number of characterizations, dependent upon three-dimensional structure, that capture molecular features in ways not requiring an alignment or superposition step for the assignment of molecular similarity. These alignment-free procedures also generate a relatively small set of three-dimensional descriptors. The descriptors are essentially mathematical terms, derived from a molecule's three-dimensional structure, that allow comparisons between molecules. These descriptors enable greater ease of statistical analysis.

Additional procedures involve molecular moments of molecules. These procedures do not require alignment. Molecular moments descriptive of some molecular property provide a small set of alignment-free descriptors that can be utilized in QSAR. For instance, there is a technique that examines moments of the shape and charge distributions of neutrally charged molecules. The molecular charge distribution is responsible for the electrostatic field external to the molecule. In this technique, a particular moment representation of the charge distribution was developed that utilized a special feature of this electrostatic field. This lead to the definition of the "center-of-dipole," about which quadrupole descriptors had been obtained. This procedure required that the zeroth-order moment or net molecular charge was identically equal to zero. By definition, this is a condition satisfied by neutrally charged molecules. This method is explained in greater detail in U.S. Pat. No. 5,784,294, "System and Method for Comparative Molecular Moment Analysis (COMMA)," the disclosure of which is incorporated herein by reference.

While the COMMA method tremendously improved drug discovery techniques, there are some areas that could be improved in this method. One area for improvement is that the method can only be used on neutral molecules. A side effect of this is that the zeroth-order moment is zero. In fact, if the zeroth-order moment is not zero, this technique cannot be used. This makes the zeroth-order moment less effective for comparison purposes. Another area for improvement on this method is that the first-order moment is invariant. This means that, regardless of from what reference the first-order moment is calculated, the first-order moment will be the same. Additionally, this technique does not generalize well to third-order and higher-order moments.

If the zeroth-order moment of the property field does not vanish, the nature of the expansion changes. For this case, neither the first nor second-order moments are invariant with respect to the choice of the origin of the expansion. This means that the moments will change depending on selection of the origin. For such expansion, the first-order or linear moment is generally non-vanishing. Linear moments of the hydrophobic property fields of alpha helical secondary structures have provided a measure of the amphiphilicity of such helices. This has been used in identifying the helical regions of proteins that bind to the surface of biological membranes. For more information on this, see Eisenberg et al., "The helical hydrophobic moment: a measure of the amphiphilicity of a helix," Nature 1982, 299, 371–374, the disclosure of which is incorporated herein by reference.

The second-order moment in the expansion about the centroid of the molecule yields second-order moments that can be written as the elements of a Weighted Holistic Invariant Molecule (WHIM) covariance matrix. For more information on WHIM, see Todeschini et al., "New 3D Molecular Descriptors: The Whim theory and QSAR Applications," 3D QSAR in Drug Design, 1998, Vol.2, Part 3, 355; and Gancia et al., "Global 3D-QSAR methods: MS-WHIM and autocorrelation," J. Comput-Aided Mol. Des. 2000, 14, 293–306, the disclosures of which are incorporated herein by reference. The centroid is generally calculated by determining the spatial locations of the atoms in a molecule and determining the center of mass for the molecule, with each atom assigned a mass of one. The WHIM covariance matrix yields a number of descriptors that can be used to compare molecules. The WHIM descriptors change if the centroid changes. Thus, the WHIM descriptors involve an explicit relationship between the property field and the underlying structure of the molecule. While the WHIM descriptors are beneficial, they are written in way that has no molecular shape frame of reference. The only reference is the centroid.

Thus, what is needed is a way of overcoming the problems of alignment, a zero zeroth-order moment, an invariant first-order moment, and an explicit relationship, between the property field and the underlying structure of the molecule.

SUMMARY OF THE INVENTION

Generally, the present invention provides and uses a set of descriptors of three-dimensional molecular property fields. A portion of the descriptors are calculated in such as way as to separate property fields from the underlying structure of the molecule. These descriptors are calculated through reference to a property field center. Thus, only if the property field changes, such as by moving an atom having a non-zero property value, will the descriptors need to be recalculated.

Additionally, a portion of the descriptors do relate to the underlying molecular structure, only these descriptors contain information from more than one reference point. In particular, a displacement is determined between a property field center and the centroid of a molecule. This descriptor contains information from two reference points. Furthermore, components of a property field are mapped onto a principal geometric frame, which essentially references the property field to the molecular shape. These descriptors thus contain information relating to the geometric frame of the molecule.

A more complete understanding of the present invention, as well as further features and advantages of the present invention, will be obtained by reference to the following detailed description and drawings.

BRIEF DESCRIPTION OF THE DRAWINGS

FIG. 5 shows binding affinities of Polychlorinated Dibenzofurans;

FIG. 7 shows a descriptor matrix, determined in accordance with one embodiment of the present invention, for the binding affinities of Dibenzo-p-dioxins;

FIG. 8 shows a correlation matrix determined from the data of FIG. 7; and

FIG. 9 shows the principal components of the set of descriptors shown in FIG. 8.

DETAILED DESCRIPTION OF PREFERRED EMBODIMENTS

Basically, the present invention provides a set of descriptors to be used in three-dimensional Quantitative Structure Activity Relations (QSAR). These descriptors allow molecules to be compared in a way that is more mathematically descriptive than are the WHIM descriptors. Some of the present descriptors are completely separate from the underlying structure of a molecule. Other descriptors in the present invention are related to the underlying structure of the molecule, but in a way that provides multiple points of reference.

Figure 1:
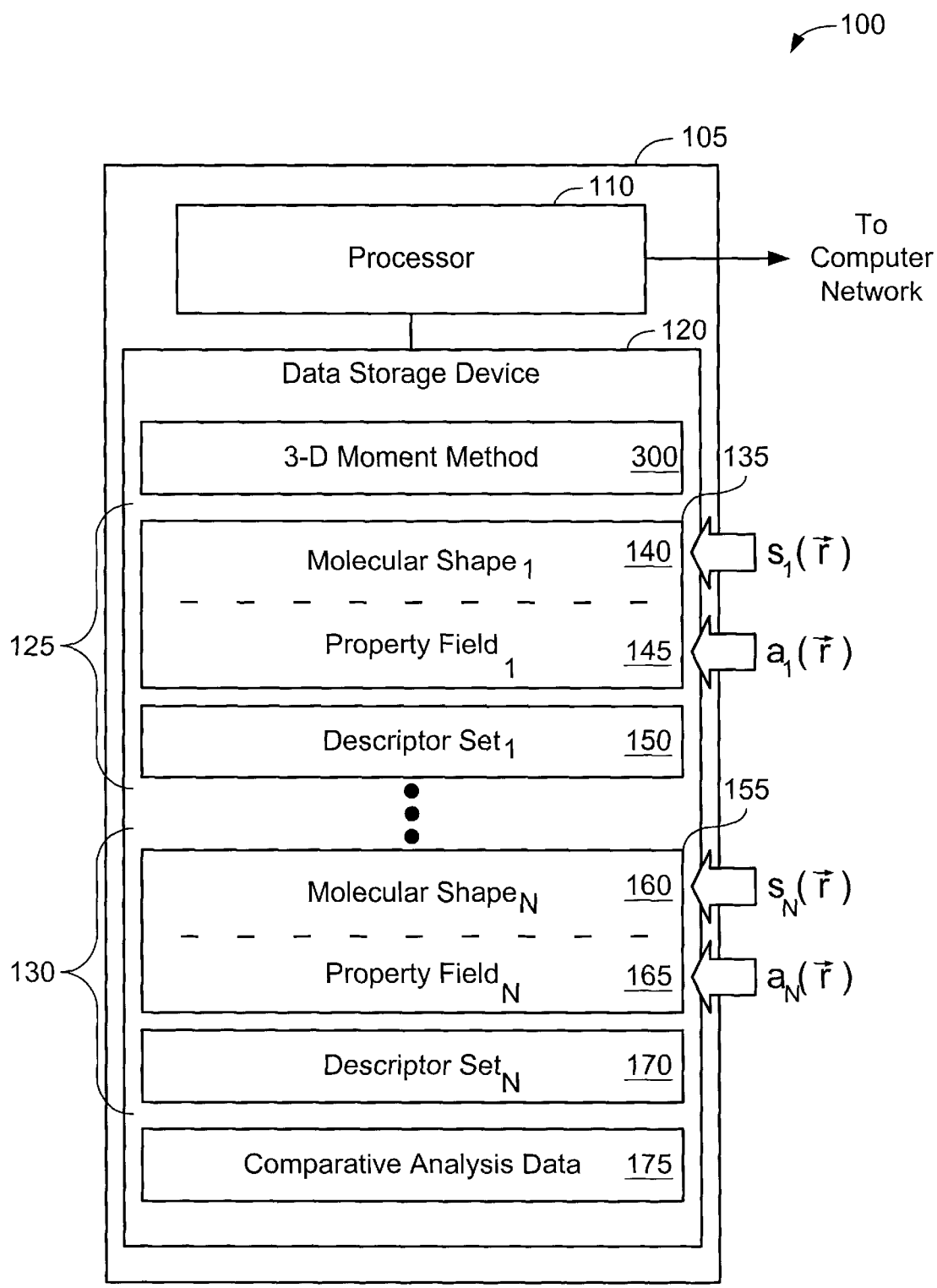
FIG. 1 is a computer system for determining and using three-dimensional moments of molecular property fields in accordance with one embodiment of the present invention.

Referring now to FIG. 1, this figure shows a block diagram of a system 100 for determining and using three-dimensional moments of molecular property fields. System 100 comprises a computer system 105 that comprises processor 110 and a data storage device 120. Data storage device 120 comprises a three-dimensional moment method 300, information from N molecules, of which information 125 from a first molecule and information 130 from the Nth molecule are shown, and comparative analysis data 175. Information 125 from the first molecule comprises property field mapping 135 and descriptor set 150. Property field mapping 135 comprises molecular shape 140 and property field 145. Similarly, information 130 from the first molecule comprises property field mapping 155 and descriptor set 170. Property field mapping 155 comprises molecular shape 160 and property field 165.

Computer system 105 comprises a processor 110 operatively coupled to the data storage device 120. Data storage device 120 will configure the processor 110 to implement the methods, steps, and functions disclosed herein. The data storage device 120 could be distributed or local and the processor 110 could be distributed or singular. The data storage device 120 could be implemented as an electrical, magnetic or optical memory, or any combination of these or other types of storage devices.

Molecular shape 140, 160 will comprise information about the shape of a molecule. Such information will normally be derived from a three-dimensional molecular density function, $s_1(\vec{r})$ or $S_N(\vec{r})$, respectively. The molecular density function is used to indicate the shape of a molecule. Molecular density is simply one way of determining molecular shape, and any function that indicates shape of a molecule may be used for molecular shape 140, 160. This molecular density function could be continuous. In this case, molecular shape 140, 160 could contain an equation or series of equations that provide a continuous function of molecular density. Such equations could describe a Connolly or van der Waals surface. Molecular shape 140, 160 could also contain a sampled version of an equation or a series of equations that describe a continuous function. In the latter example, molecular shape 140, 160 would then contain discrete points at particular three-dimensional locations. Generally, however, the molecular density function will usually contain three-dimensional locations that indicate the center of atoms in the molecule. Such information may or may not include mass information. Thus, molecular shape 140, 160 will, in general, contain the same three-dimensional locations.

Property field 145, 165 will contain information about the property being examined. Such properties could include, for example, mass or density, hydrophobicity, or binding affinities. Property field 145, 165 will, in general, be described by a scalar molecular property field density such as or $a_N(\vec{r})$, respectively. The scalar molecular property field density can be either continuous or discrete.

Figure 2:
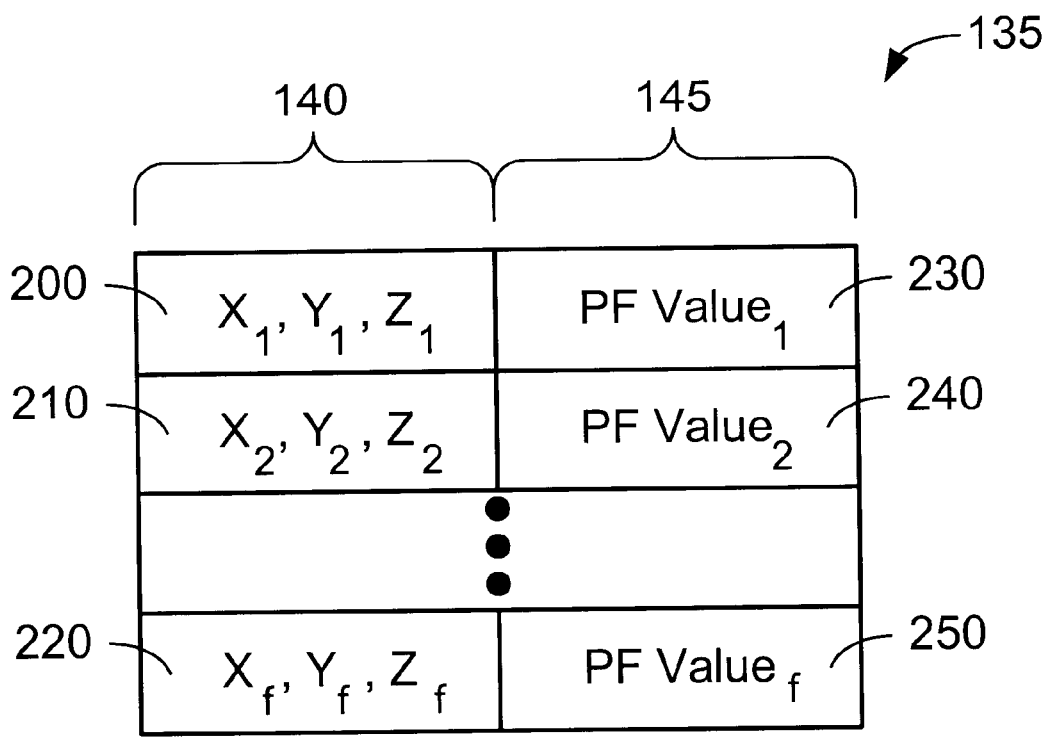
FIG. 2 illustrates a property field mapping, comprising shape and property field information, for a molecule in accordance with one embodiment of the present invention.

Molecular shape 140 can be stored separately from property field 145. However, normally these are stored together such that each three-dimensional point in molecular shape 140 will contain an equivalent property value of the property field at that point. Thus, molecular shape 140 and property field 145 will usually be stored as property field mapping 135. An exemplary property field mapping 135 is shown in FIG. 2.

Similarly, molecular shape 160 can be stored separately from property field 165. However, these will normally be stored together as property field mapping 155.

It should be noted that the example of FIG. 1 shows only one property field mapping for each molecule. There could be multiple property field mappings for each molecule. Each additional property field mapping will generally contain one molecular shape and multiple property fields, with each property field described by another molecular property field density. Usually, each property field mapping will contain a point in a three-dimensional space, followed by several property values for different property fields. For example, at a three-dimensional point$_1$, there could be a mass of $M_1$ and a hydrophobicity of $H_1$; at a three-dimensional point$_2$, there could be a mass of $M_2$ and a hydrophobicity of $H_2$.

Three-dimensional moment method 300 uses the information in property field mapping 135, 155 to create sets of descriptors 150, 170, respectively. Descriptors 150, 170 are mathematical values that each represent some feature of a molecule. The descriptors in the present invention use three-dimensional moments to determine their values. These descriptors can then be compared and comparative analysis data 175 determined. Comparative analysis data 175 can be used to determine similarities between molecules. Such comparative analysis are common in drug discovery and other fields.

It should be noted that each property field will generally equate with one descriptor set. Consequently, if there are five property fields for a single molecule, there will generally be five descriptor sets for this molecule.

Thus, FIG. 1 shows a system that can take molecular shape and property field data, determine descriptors from this data, and use the descriptors to compare molecules.

Turning now to FIG. 2, this figure shows an exemplary property field mapping 135. Property field mapping 135 is organized into two columns, molecular shape 140 and property field 145. Molecular shape 140 comprises elements 200, 210, 220, each of which contains the X, Y, Z coordinates of the center of an atom in a molecule. Corresponding to each of these elements 200, 210, 220 are property field values 230, 240, 250, respectively. Therefore, there is one property field value for each coordinate. Generally, these coordinates are given in an arbitrary reference frame. There is usually no effort to coordinate the reference frame of one molecule with the reference frame of another molecule.

It should be noted that property field mapping 135 may comprise additional data, not shown in FIG. 2. For example, the type of atom at each point could be given. This would allow certain properties, such as mass, to be derived from the atom information. Additional property field values can be added by columns. For instance, a third column could be added that contains elements for another property field. Each element in the third column would then contain the property field value that corresponds to one of the elements 200, 210, 220. For each element 200, 210, 220, there would then be corresponding property field values for multiple property fields.

Figure 3:
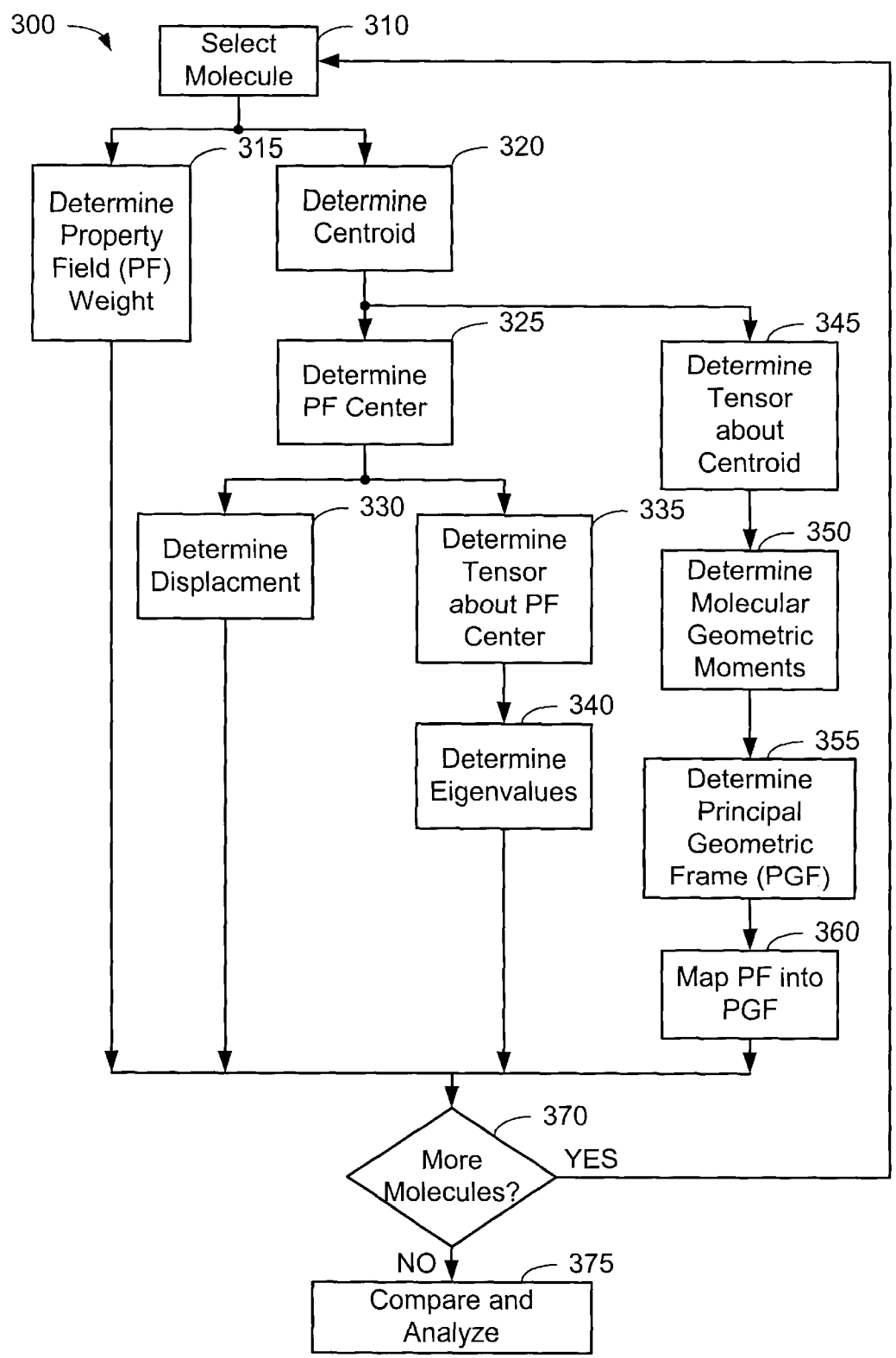
FIG. 3 illustrates a flow chart of a method for determining and using three-dimensional moments of molecular property fields in accordance with one embodiment of the present invention.

Referring now to FIG. 3, this figure shows a flow chart of an exemplary method 300 for determining and using three-dimensional moments of molecular properties. Although it is possible to perform method 300 on a single molecule, this method is preferably performed whenever two or more molecules will be compared. Usually, there will be molecular shape and property field data from multiple molecules residing in a memory of a computer. From this data, method 300 will determine the preferred descriptors of the present invention (and, optionally, other descriptors) and use these descriptors to compare molecules. Note that method 300 shows the determination of descriptors for only one property field; the method may easily be modified to create a set of descriptors for each of a number of property fields.

Method 300 begins in step 310 when a particular molecule is selected. Method 300 may be traversed in a number of ways and many of the steps may be performed in parallel. The following discussion will traverse method 300 in a particular manner; however, other series of steps would be equally as good.

In step 315, a property field weight is determined from molecular shape and property field data. The property field weight is one of a set of descriptors that will be used to compare molecules. In step 320, a centroid of a molecule is determined. As previously discussed, a centroid is equivalent to the center of mass when each atom is given a unit mass. In the discussion below, equations for a property field weight and a centroid will be discussed for arbitrary property fields and molecular shapes, and then a more specific example will be developed.

To determine a property field weight, a molecular moment is calculated. In general terms, if $a(\vec{r})$ is a defined scalar molecular property field density that can adopt positive or negative values over the three-dimensional molecular density distribution, $s(\vec{r})$, the zeroth and first-order moments can be written as:

$$m_0 = \int a(\vec{r}) s(\vec{r}) d\vec{r} \quad \text{(Eq. 1)}$$

$$\vec{m}_1 = \int a(\vec{r}) s(\vec{r}) \vec{r} d\vec{r} \quad \text{(Eq. 1)}$$

The $m_0$ moment may be thought of as the property field weight (step 315). Moments of the molecular density distribution are obtained for a property field density $a(\vec{r})$ set equal to unity. Consequently, the location of the molecular centroid (step 320) is given by:

$$\vec{r}_c = \frac{\int \vec{r} s(\vec{r}) d\vec{r}}{\int s(\vec{r}) d\vec{r}} \quad \text{(Eq. 3)}$$

The property field distribution is arbitrary. However, it is assumed that these, as well as subsequent integrals or sums, are well defined.

In a general sense, the functional form of $s(\vec{r})$ could be chosen to delineate a Connolly or van der Waals surface. For such choice, the property field values, $a(\vec{r})$, would be mapped to such surface. The example developed below, however, assigns property field values, $a_i$, to the atom centers only. The function $s(\vec{r})$ is then the set of Dirac delta functions, δ, centered at each of the atomic sites, i. The total number of atoms, n, composing the molecule can be written:

$$n = \int s(\vec{r})d\vec{r} = \int \sum_i \delta(\vec{r} - \vec{r}_i)d\vec{r} \qquad \text{(Eq. 4)}$$

The zeroth and first-order property field moments are then written:

$$m_0 = \sum_i a_i \qquad \text{(Eq. 5)}$$

$$\vec{m}_1 = \sum_i a_i \vec{r}_i \qquad \text{(Eq. 6)}$$

As previously discussed, $m_0$ is called the property field weight (step 315). Therefore, if the property field values are the atomic masses, $m_0$ will be the molecular weight. If the property field values are, for example, the Ghose-Crippen atomic hydrophobicity values, $m_0$ will be the logarithm of the partition function, or Log P. For more information on Ghose-Crippen atomic hydrophobicity values, see Ghose et al., "Atomic Physicochemical Parameters for Three-Dimensional Structure-Directed Quantitative Structure-Activity Relationships I, Partition Coefficients as a Measure of Hydrophobicity," J. Comput. Chem. 1986, 7, 565–577, the disclosure of which is incorporated herein by reference.

Since the zeroth-order moment of the expansion is non-vanishing, $\vec{m}_1$, the first-order moment, is not invariant to the choice of origin. Eisenberg proposed the use of such a first-order moment in connection with amino acid hydrophobic property values for the determination of the amphipathicity of the alpha helices of membrane bound proteins. For more on the method of Eisenberg, see Eisenberg et al., "The helical hydrophobic moment: a measure of the amphiphilicity of a helix," Nature 1982, 299, 371–374. In the method proposed by Eisenberg, vector components were calculated from the alpha carbon to the centroid of the residue under consideration or from the axis of the helix to the alpha carbon of the residue. This provided a net vector essentially perpendicular to the helical axis. It was also stated that one might use the following hydrophobic vector, invariant with respect to the choice of origin of expansion, to provide a component along the helical axis as well:

$$\vec{m}_1 = \sum_i (a_i - \bar{a})\vec{r}_i \qquad \text{(Eq. 7)}$$

with $\bar{a}$ equal to what will be called the property field mean:

$$\bar{a} = \frac{1}{n}\sum_i a_i = \frac{m_0}{n} \qquad \text{(Eq. 8)}$$

The vector in Equation 7 is then descriptive of first-order deviations about, $\bar{a}$, the average over the n amino acid residue helix. This is equivalent to referencing the property field vector to the centroid of the structure, $\vec{r}_c$, namely, $$\vec{m}_1 = \sum_i a_i(\vec{r}_i - \vec{r}_c) \qquad \text{(Eq. 9)}$$

with $$\vec{r}_c = \frac{1}{n}\sum_i \vec{r}_i \qquad \text{(Eq. 10)}$$

Equation 10 calculates the centroid for this simpler example (step 320). The vector, $\vec{m}_1$, will have a component perpendicular to the helical axis as well as one along the axis. As a molecular descriptor, such vector would therefore characterize the first-order difference in property field distribution about the property field mean.

The integral representation of the moments in equations 1 and 2 that referenced the property field distribution, $a(\vec{r})$, to the molecular density distribution, $s(\vec{r})$, enables one to retain the equivalence between the integral representations of Equations 7 and 9. Without such mapping, this equivalence would no longer hold.

Second-order moments of the property field about the centroid can be defined as components of the following second-rank tensor:

$$\tilde{m}_2^c = \sum_i a_i(\tilde{1}|\vec{r}_i - \vec{r}_c|^2 - (\vec{r}_i - \vec{r}_c)(\vec{r}_i - \vec{r}_c)) \qquad \text{(Eq. 11)}$$

where 1 is the unit dyadic. The superscript $^c$ indicates that the moment is calculated about the molecular centroid. This tensor will be used in subsequent steps of method 300.

Had the second rank tensor been chosen as:

$$\tilde{m}_2^c = \sum_i a_i(\vec{r}_i - \vec{r}_c)(\vec{r}_i - \vec{r}_c) \qquad \text{(Eq. 12)}$$

it would be the same as the WHIM covariance matrix, aside from a normalizing factor. The principal-axes of Equations 11 and 12 are identical. However, the eigenvalues of Equation 12 are linear combinations of the moments-of-geometry, while the eigenvalues of Equation 11 are the moments-of-inertia for a molecule with property field values of unit mass assigned at each of the atomic sites. Since the eigenvalues of Equation 11 and Equation 12 are linearly related, they will yield identical results when used as descriptors in a multilinear regression.

Property field descriptors can also be obtained by moment expansions about the property field center. Early WHIM descriptors were obtained by an expansion about such origin. Moments-of-inertia would be obtained as the eigenvalues of Equation 11 for a property field that assigned the atomic mass to the atom centers and the expansion performed about the center-of-mass. As discussed in more detail below, the center-of-mass may be thought of as property field center of the mass distribution. More generally, the choice of Equation 11 assigns the eigenvalues of all property-fields as radial property field distributions that are normal to each of the corresponding principal-axes. This is in analogy with the relationship between the moments-of-inertia and their corresponding principal-axes.

The property field center is determined in step 325 of method 300. The centroid (as discussed above in reference to step 320) is defined as the origin of the moment expansion for which the first-order moment of the molecular density distribution vanishes. In other words, it is the property field center of this density distribution. This distribution is generally simply chosen by assigning unit property values at each atomic center.

Since moment expansions can be performed about an arbitrary origin, one can expand property fields about the property field center in analogy with expansions performed about the center of mass. The property field center is obtained by translating the origin of expansion to the location about which the first-order property field moment vanishes. Thus, in step 325, the property field center, $\vec{a}$, is determined by determining at which point the first-order property field moment will be zero. One way of determining this location is to use Equation 13, given below, to determine a vector in a current three-dimensional coordinate system. The origin of the current three-dimensional coordinate system may then be translated by this vector, which puts the new origin at the property field center.

Displacement to the property field center, $\vec{a}$, from an arbitrary location is given by:

$$\vec{a} = \frac{\sum_i a_i \vec{r}_i}{\sum_i a_i} \tag{Eq. 13}$$

The property field values in Equation 13 need not be positive. However, the property field weight, namely the zeroth-order moment of the expansion, must differ from zero. For property values of varying sign, this center might not be proximate to the molecule. Furthermore, as the property field weight goes to zero, the distance of the property field center from any arbitrary origin at which the calculation is performed will increase without limit. This is similar to the behavior of the location of the center-of-dipole as the dipole of a neutrally charged molecule becomes vanishingly small. The property field center of molecular charge, namely, the "center-of-charge" has been previously utilized and has provided a useful reference in distinguishing the electrostatic from the inertial properties of an ion. For more information on use of the center-of-charge, see Herman, "Center of Dispersion Force in HCL Interacting with Rare-Gas Atoms," The Journal of Chemical Physics 1966, 44, 1346–1352; and Vegh, "Scattering correlation in double ionization of helium by fast antiprotons and protons," Physical Review A 1988, 37, 992–994, the disclosures of which are incorporated by reference.

The first-order property field moments then vanish about the property field center, and one can define second-order moments of the property field about this center that comprise the following second rank tensor, determined in step 335 of method 300:

$$\tilde{m}_2^P = \sum_i a_i(\tilde{1}|\vec{r}_i - \vec{a}|^2 - (\vec{r}_i - \vec{a})(\vec{r}_i - \vec{a})) \tag{Eq. 14}$$

The superscript $^P$ indicates that the moments are calculated about the property field center.

Just as the moments-of-geometry, $I_x^g$, $I_y^g$, $I_z^g$, can be utilized as descriptors of molecular shape, the property field eigenvalues of Equation 14 can be utilized as descriptors of the molecular property field distribution. For property field values at the atomic sites that are either positive or negative, the matrix of Equation 14 will be real and symmetric. Hence, the matrix will be Hermitean, which guarantees real eigenvalues, $\Theta_1$, $\Theta_2$, $\Theta_3$. These real eigenvalues are calculated in step 340 of method 300, and they may be calculated through means well known to those skilled in the art, such as through diagonalization of Equation 14. The eigenvalues, $\Theta_1$, $\Theta_2$, $\Theta_3$ are added to $m_0$ as the descriptors of the present invention.

The magnitude of the displacement between the molecular centroid and property field center provides one further molecular descriptor. This descriptor incorporates information that had apparently been lost in the expansion about the property field center. This displacement, $\vec{d}$, can be written (step 330 of FIG. 3):

$$\vec{d} = \vec{a} - \vec{r}_c = \frac{\vec{m}_1}{m_0} \tag{Eq. 15}$$

Therefore, information provided by the first-order moment, $\vec{m}_1$, in the expansion about the molecular centroid is retained by including the displacement, $\vec{d}$, as a descriptor for expansions performed about the property field center for which the first-order moment vanishes. For the property field of molecular charge, the displacement of the center-of-charge with respect to the center-of-mass has assisted in the prediction of the electrophoretic mobilities of peptides. For more information on this prediction method, see Metral et al., "A Computer method for predicting the electrophoretic mobility of peptides," HRC-Journal of High Resolution Chromatography, 1999, 22, 373–378.

Thus, steps 315 through 340 determine moments of the property field about the property field center and yield the following five molecular descriptors:

$$m_0, |\vec{d}|, \Theta_1, \Theta_2, \text{ and } \Theta_3$$

with $|\vec{d}|$ the magnitude of $\vec{d}$. Moments have been used within the context of the spatial pattern recognition of two and three-dimensional objects. In principle, one is not limited to a consideration of only the first three lowest order moments for the purposes of comparison. The principal-axes of Equation 14 provide a reference set of axes for calculation of and comparison between higher order moments. The present invention allows moments above the second-order moments to be calculated. For more information on using moments for spatial pattern recognition, see Taubin et al., "Representing and Comparing Shapes Using Shape Polynomials," IEEE Conference on Computer Vision and Pattern Recognition, CVPR'89, 1989, 510–516; and Duda et al., "Pattern Classification and Scene Analysis," Wiley; New York, 1973, Chapter 9, 364, the disclosures of which are incorporated herein by reference.

Shape descriptors of the molecule can also be included by adding the molecular geometric moments, $I_x^g$, $I_y^g$, $I_z^g$ to the set of descriptors of the present invention. To determine the geometric moments, first Equation 11 is performed with $a_i$ set to unity. A tensor, determined about the centroid, is determined in step 345. This tensor can be diagonalized, and the diagonal entries of the resultant matrix will be the molecular geometric moments, $I_x^g$, $I_y^g$, $I_z^g$. These are determined in step 350. As is known in the art, these molecular geometric moments are also the eigenvalues of the matrix defined by Equation 11 with $a_i$ set to unity, and they can be determined in ways other than through diagonalization.

Although the eigenvalues of Equation 11 with $a_i$ set to unity may be determined through other methods, diagonalization provides an additional benefit in this instance. Diagonalization of the second-rank property field tensor composed of moments of the molecular density distribution, $s(\vec{r})$, provides the set of principal geometric axes that can be used to reference other property field vectors or tensor components to molecular shape. This occurs in step 355 of method 300. One way of determining the principal geometric axes is by calculating a matrix P such that $P^{-1}AP$ is diagonal, where A is the second-rank property field tensor composed of moments of the molecular density distribution, $s(\vec{r})$. The matrix P then is a rotation matrix that rotates the original three-dimensional frame to the principal geometric frame. A simple description of diagonalization is given in Anton, "Elementary Linear Algebra, Fifth Edition," John Wiley and Sons, 1987, 309–316, the disclosure of which is incorporated herein by reference. A set of moment descriptors that is invariant to the sensing of the principal geometric axes are the diagonal components of the second-order property field tensor written in the principal geometric frame, namely, $Q_{xx}^c$, $Q_{yy}^c$, $Q_{zz}^c$. These can be determined through the following equations:

$$Q_{xx}^c = \sum_i a_i((y_i - y_c)^2 + (z_i - z_c)^2) \quad \text{(Eq. 16)}$$

$$Q_{yy}^c = \sum_i a_i((x_i - x_c)^2 + (z_i - z_c)^2) \quad \text{(Eq. 17)}$$

$$Q_{zz}^c = \sum_i a_i((x_i - x_c)^2 + (y_i - y_c)^2) \quad \text{(Eq. 18)}$$

These equations essentially map (step 360 of FIG. 3) the property field onto the principal geometric frame. These are additional descriptors to be added to the descriptors of the present invention. The origin of the coordinate system of Equations 16 through 18 is chosen at the molecular centroid as indicated by the superscript, $^c$, and the axes are aligned with the principal geometric axes. Other vector and tensor components can be written that would not be invariant to the sensing of the axes unless magnitudes of the components were used or some additional referencing invoked to provide the sensing.

Recapitulating, the set of eleven descriptors of the present invention are shown below:

$I_{xg}$, $I_{yg}$, $I_{zg}$, $m_0$, $|\vec{d}|$, $Q_{xx}^c$, $Q_{yy}^c$, $Q_{zz}^c$, $\Theta_1$, $\Theta_2$, and $\Theta_3$.

These will be used in the calculations described in the next section. This set of descriptors will be named CoMMA2 to distinguish it from the CoMMA set developed for the charge distribution of neutrally charged molecules.

Once these descriptors are determined for one molecular and one property field of that molecule, in step 370 it is determined whether there are any additional molecules that have to have their descriptors determined. If there are, then steps 310 through 360 are performed again. If there are no more molecules, then step 375 is performed.

In step 375, a descriptor from one molecule is compared against a descriptor of another molecule. The purpose of such comparisons is to determine whether two molecules are similar, because similar molecules should behave similarly. Because the descriptors will be numbers, statistical analysis may be performed on these numbers to determine similarity between molecules. Additionally, it is also possible to statistically determine if the descriptors themselves correlate with biological activity. For instance, it could be determined if the set of descriptors $Q_{xx}^c$, $Q_{yy}^c$, $Q_{zz}^c$ relate to biological activity. Such statistical analysis is well known to those skilled in the art, and some exemplary statistical analysis will be discussed in reference to the "EXAMPLES" section below.

Note that either immediately before or immediately after step 370 would be ideal locations to add a step to include additional property fields. For example, if there is another property field that needs its set of descriptors determined, these descriptors could be determined prior to step 370 (for a single molecule) or after step 370 (for all molecules).

Thus, FIGS. 1 through 3 provide a method and apparatus that determine descriptors based on three-dimensional moments of molecular property fields. Some of the descriptors are completely separate from the underlying molecular structure. Other descriptors relate the property field to the underlying molecular structure, but relate these two in a way not previously done. In particular, these methods use multiple reference points.

As is known in the art, the methods and apparatus discussed herein may be distributed as an article of manufacture that itself comprises a computer readable medium having computer readable code means embodied thereon. The computer readable program code means is operable, in conjunction with a computer system such as computer system 105 of FIG. 1, to carry out all or some of the steps to perform the methods or create the apparatus discussed herein. The computer readable medium may be a recordable medium (e.g., floppy disks, hard drives, compact disks, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic media, or height variations on the surface of an optical disk.

EXAMPLES

The hydrophobic atom fragment assignments of Ghose and Crippen were used in a QSAR analysis of the binding affinity of seventy-four polyhalogenated aromatic compounds to the Ah cystolic receptor. The moments provide a simple three-dimensional description of the property field of molecular hydrophobicity and expand this important scalar field into the realm of three-dimensions. This particular set of molecules has been chosen since a number of previous QSAR studies have been performed with the original binding data. For instance, see Wagener et al., "Autocorrelation of Molecular Surface Properties for Modeling Corticosteroid Binding Globulin and Cystolic Ah Receptor Activity by Neural Networks," J. Am. Chem. Soc. 1995, 117, 7769–7775; Clementi et al., "Autocorrelation as a tool for a congruent description of molecules in 3D-QSAR studies," Pharm. Pharmacol. Lett. 1993, 3, 5–8; Waller et al., "Comparative Molecular Field Analysis of Polyhalogenated Dibenzo-p-dioxins, Dibenzofurans, and Biphenyls," J. Med. Chem. 1992, 35, 3660–3666, the disclosures of which are incorporated by reference. Furthermore, the calculation of LogP (the logarithm of the partition function) from atom fragment assignments has had a long and interesting history. For this history, see Livingstone, "The Characterization of Chemical Structures Using Molecular Properties: A Survey," J. Chem. Inf. Comput. Sci. 2000, 40, 195–209; Abraham, et al., "Hydrophobic Fields in 3D QSAR in Drug Design, Theory, Methods, and Applications," Escom: Leiden, 1993, Part III. 3D QSAR Models, 506, the disclosures of which are herein incorporated by reference. Subsequent to the introduction of Comparative Molecular Field Analysis (CoMFA), three-dimensional hydrophobic fields were introduced to supplement the steric and electrostatic interactions of the original CoMFA implementation. See Kellogg et al., "HINT: A new method of empirical hydrophobic field calculation for CoMFA," J. Comput-Aided Mol. Des. 1991, 5, 545–552, the disclosure of which is incorporated herein by reference. The three-dimensional hydrophobic moments and related quantities of the present paper might be thought of as an intermediate characterization of hydrophobicity. The calculation is intermediate with respect to the characterization by one single number such as LogP and to the more detailed spatial three-dimensional field mapping of Hydropathic INTerations (HINT).

Figure 4:
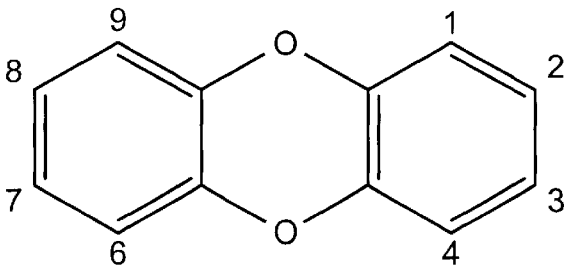
FIG. 4 shows binding affinities of Polyhalogenated Dibenzo-p-dioxins.
Figure 6:
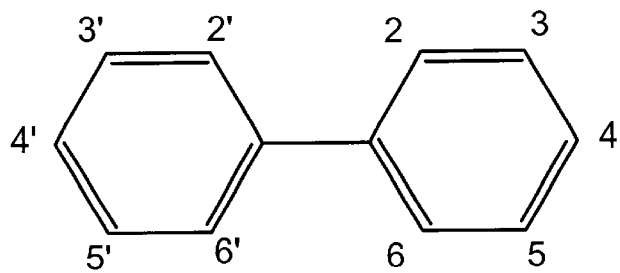
FIG. 6 shows binding affinities of Polychlorinated Biphenyls.

The seventy-four molecules (FIGS. 4 through 6) consist of three different series. FIGS. 4 through 6 show different molecules and their affinities. This series has twenty-five polychlorinated and polybrominated dibenzo-p-dioxins, thirty-five polychlorinated dibenzofurans, and fourteen polychlorinated biphenyls. The structures were determined by the TRIPOS Sybyl force field. For a more information on the latter, see Clark et al., "Validation of the Tripos 5.2 Force Field," J. Comput. Chem. 1989, 10, 982–1012, the disclosure of which is herein incorporated by reference. Ghose-Crippen fragment assignments replaced the SYBYL atom type assignments in the mol2 files and a MATLAB (a numerical analysis program made by The Mathworks Inc., 24 Prime Park Way, Natick, Mass. 01760) program was used to calculate the molecular moment descriptors of each of the molecules. The biphenyls were the only series of molecules that were non-planar. FIG. 7 lists the calculated descriptor values for the set of twenty-five dibenzo-p-dioxins.

Regression (performed with the Matlab Statistics Toolbox of MATLAB, The Mathworks Inc., 24 Prime Park Way, Natick, Mass. 01760) with no validation yielded, $r^2=0.820$ with $F=25.8$. Interestingly, the only regression coefficient with a 95% confidence interval that does not cross zero is the coefficient of the fourth descriptor, $m_0$, or the calculated LogP value. On the other hand, the LogP descriptor alone yields, $r^2=0.135$ with $F=11.3$.

Eliminating the descriptors of this correlated set (see FIG. 8) is of interest. However, this highlights the difficulty of assigning relative importance to the individual correlated descriptors. For instance, retaining only $I_x^g$, $Q_{xx}$, and $Q_{zz}$, yields $r^2=0.759$ with $F=73.2$. However, retaining only $m_0$, $\Theta_1$, and $\Theta_3$, yields $r^2=0.746$ with $F=50.6$. One expects that a molecular series of lower symmetry with hydrophobic substituent values that exhibited greater diversity would yield reduced correlation between the eigenvalues obtained about the property field center and the second-order components calculated with respect to the principal geometric axes. The significant amount of correlation for this data set has resulted since the majority of the molecules are planar. Planar molecules yield eigenvalues linearly related as exhibited in FIG. 7. A similar table (not shown) for the biphenyls does not exhibit this linear relationship.

Centering the descriptor matrix about each of the column means and normalizing by the column standard deviations yields the principal components shown in FIG. 9. Retaining only the first four principal components, accounting for 97% of the variance of the data, yields $r^2=0.542$ with $F=20.4$. Retaining the first two principal components as well as the fifth accounts for 84% of the data and yields, $r^2=0.745$ with $F=68.1$. Retaining only principal components accounting for the major variance of the data of a set of descriptors of mixed physical and chemical character normalized in this standard manner has been previously described as a strategy of questionable significance. Finally, a partial least squares (PLS) cross-validation leave-one-out calculation yields $r^2=0.760$ with nine components. Of the three series, the correlation for the biphenyls was poorly predictive, which was also found in Waller et al., "Comparative Molecular Field Analysis of Polyhalogenated Dibenzo-p-dioxins, Dibenzofurans, and Biphenyls," J. Med. Chem. 1992, 35, 3660–3666, the disclosure of which is incorporated herein by reference. Eliminating the fourteen biphenyl molecules from the cross-validated leave-one-out PLS calculation yields $r^2=0.772$ with eight components for the remaining sixty molecules. Since all sixty molecules are then planar, elimination of linearly dependent descriptors reduces the eleven to eight and hence all descriptors are retained in the PLS calculation. Apparently, the amount of information provided since the eight descriptors are not completely correlated contributes to an increase in the $r^2$. Eight components are not necessary to yield significant correlation. Five components will yield an $r^2=0.734$ for the sixty molecules.

Advantages

The present invention has addressed some of the formal issues involved in obtaining three-dimensional moments of molecular property-fields. Expansions that involve spatially distributed properties that sum to a finite value, i.e., with a non-vanishing zeroth-order moment, contrast with expansions for which this moment vanishes. For the former case, all moments above zeroth-order are dependent upon the origin of expansion.

As a consequence, attention has focused on the two centers of expansion previously identified. These are the molecular centroid and what has been defined as the property field center. Moment expansions about the molecular centroid have been shown to yield first-order and second-order terms of the expansion that can be written in a form of the Eisenberg hydrophobic moment vector and the WHIM covariance matrix, respectively.

Molecular expansions about the property field center yield a three-dimensional matrix descriptive of only the property field distribution and not explicitly descriptive of the underlying molecular shape. Thus, the present invention contrasts with WHIM. This distinction is seen simply by the following hypothetical example. Assume that the property distribution remains constant as the underlying molecular structure is changed, perhaps by displacing the atom positions slightly. For property field values assigned to the atomic sites, this can arise simply if the only atoms displaced are those assigned vanishing, or zero, property field values. The second-order moments calculated about the property field center and consequently the eigenvalues of matrix composed of these components would remain unchanged. This is a simple consequence of the invariance of the property field center to any changes in the underlying molecular structure that are not reflected in changes of the property field distribution. Note the contrast between such behavior and the modifications introduced into the second rank tensor, or WHIM covariance matrix calculated about the molecular centroid. Since the centroid is displaced, the components of this matrix will change even though the property field distribution has remained unchanged. The WHIM descriptors, therefore, do involve an explicit description of the relationship between the property field and the underlying molecular structure.

Since expansion about the property field center, as performed in the present invention, does not include such explicit relationship, such relationship has been introduced in a different and better manner. Additional descriptors involving second-order moments written in the frame of the principal geometric axes are introduced. Such moments include information that relates the property field to not only the location of the molecular centroid, but to the orientation of the molecular principal geometric axes as well. While it is certainly true that a modification in molecular structure will generally be accompanied by a modification of the property field, it is important to recognize that the two distributions are different if one is to develop systematic relationships between them, such as those developed with this invention.

Expansion about the property field center provides the further capability of generating moment expansions to arbitrary order for the purposes of property field moment comparisons. This is achieved by use of the property field principal axes obtained in second-order as a frame of reference for higher order. Recognition of chiral differences will, however, require a procedure that senses the principal axes.

Finally, the set of moment descriptors and related quantities proposed have been utilized in a QSAR with respect to the binding of seventy-four polyhalogenated aromatic molecules to the Ah cystolic receptor. The hydrophobic property field moments provide descriptors that yield correlations that are as statistically significant as have been achieved previously.

It should be emphasized that the present invention could be applied to any number of different property-fields simultaneously. For example, one might take grid based electrostatic and steric values of CoMFA as two property-fields and the grid based hydrophobicity values of HINT as a third. Sums over the grid points would then yield moments with respect to the different distributions as well as moments and other quantities that related the distributions. While there would, of course, be a significant loss of detailed information, for a QSAR one would gain translation from a highly underdetermined statistical problem to one that was overdetermined with loss of the required molecular alignment step. Many options are, therefore, open with respect to the use of moments.

It is to be understood that the embodiments and variations shown and described herein are merely illustrative of the principles of this invention and that various modifications may be implemented by those skilled in the art without departing from the scope and spirit of the invention. For instance, the molecular shape could be described by a van der Waals, Connolly, or other surface instead of being described by points at the center of atoms of a molecule.

What is claimed is:

1. A computer-based method for determining three-dimensional moments of molecular property fields, the method comprising the steps of:

for a given molecule within a series of molecules:
storing in memory first data representing a shape of the given molecule at points in a first coordinate system;
storing in memory second data representing a spatial distribution of a property of the given molecule in the first coordinate system;
determining a centroid of the given molecule based upon the first data;
identifying a property center in the first coordinate system wherein a first order moment of the spatial distribution of the property represented by the second data is zero; and
determining a displacement between the centroid and the property center.

2. The method of claim 1, wherein the first data is derived from a continuous molecular density function that describes the given molecule and wherein each atom in the molecular density function is assigned a mass of one to determine the centroid.

3. The method of claim 1, wherein the first data is derived from a molecular density function having densities only at centers of atoms of the given molecule and wherein each atom in the molecular density function is assigned a mass of one to determine the centroid.

4. The method of claim 1, further comprising the step of determining a magnitude of the displacement.

5. The method of claim 4, further comprising the steps of:
performing the method for at least two molecules; and
comparing a magnitude of a displacement of one of the molecules with a magnitude of a displacement of another of the molecules.

6. The method of claim 1, further comprising the step of determining a plurality of descriptors that characterize the property of the given molecule, wherein the displacement is one of the plurality of descriptors.

7. The method of claim 6, further comprising the step of defining a first second-rank tensor that defines second order moments of a spatial distribution of the property about the property center.

8. The method of claim 7, wherein the method further comprises the step of determining a set of eigenvalues associated with the first second-rank tensor, and wherein the plurality of descriptors further comprise the set of eigenvalues.

9. The method of claim 8, further comprising the steps of:
determining a second second-rank tensor that defines second order moments of the spatial distribution of the property about the centroid, wherein each value of the property is assigned a value of one; and
mapping the spatial distribution of the property of the given molecule onto a set of principal geometric axes determined by using the first second-rank tensor.

10. The method of claim 9, wherein the step of mapping comprises the steps of:
diagonalizing the second second-rank tensor;
determining, from diagonalizing of the second second-rank tensor, a new coordinate frame; and
using the new coordinate frame to map the spatial distribution of the property of the given molecule onto the set of principal geometric axes determined by the new coordinate frame.

11. The method of claim 10, wherein the set of principal geometric axes comprises three principal geometric axes, wherein the mapping generates three invariant components, and wherein the plurality of descriptors further comprises the three invariant components.

12. The method of claim 9, further comprising the step of determining a property field weight, wherein the property field weight is another of the plurality of descriptors.

13. The method of claim 6, further comprising the steps of:
defining a second second-rank tensor that defines second order moments of a spatial distribution of the property about the property center, wherein each value of the property is assigned a value of one; and
diagonalizing the second second-rank tensor;
selecting diagonal entries of the second second-rank tensor as being molecular geometric moments, wherein the plurality of descriptors further comprises the molecular geometric moments.

14. A computer-based method for determining three-dimensional moments of molecular property fields, the method comprising the steps of:
for a given molecule within a series of molecules;

storing in memory first data representing a shape of the given molecule at points in a first coordinate system;

storing in memory second data representing a spatial distribution of a property of the given molecule in the first coordinate system;

determining a centroid of the molecule;

determining a first second-rank tensor that defines second order moments of the spatial distribution of the property about the centroid, wherein each value of the property is assigned a value of one; and mapping the spatial distribution of the property of the given molecule onto a set of principal geometric axes determined by using the first second-rank tensor.

15. The method of claim 14, wherein the set comprises one principal geometric axis.

16. The method of claim 14, wherein the set comprises three principal geometric axes.

17. The method of claim 14, wherein the step of mapping comprises the steps of:

diagonalizing the first second-rank tensor;

determining, from diagonalizing the first second-rank tensor, a new coordinate frame; and using the new coordinate frame to map the spatial distribution of the property of the given molecule onto the set of principal geometric axes determined by the new coordinate frame.

18. The method of claim 14, wherein the set of principal geometric axes comprises three principal geometric axes and wherein the mapping generates three invariant components.

19. The method of claim 18, wherein the method further comprises the steps of:

performing the method for at least two molecules; and comparing each of the three invariant components from one of the at least two molecules with a corresponding one of the three invariant components of another of the at least two molecules.

20. A system for determining three-dimensional moments of molecular property fields, the system comprising:

a memory that stores computer-readable code; and a processor operatively coupled to the memory, the processor configured to implement the computer-readable code, the computer-readable code configured to, for a given molecule within a series of molecules:

store in the memory first data representing a shape of the given molecule at points in a first coordinate system;

store in the memory second data representing a spatial distribution of a property of the given molecule in the first coordinate system;

determine a centroid of the given molecule based upon the first data;

identify a property center in the first coordinate system wherein a first order moment of the spatial distribution of the property represented by the second data is zero; and determine a displacement between the centroid and the property center.

21. The system of claim 20, wherein the first data is derived from a continuous molecular density function that describes the given molecule and wherein each atom in the molecular density function is assigned a mass of one to determine the centroid.

22. The system of claim 20, wherein the first data is derived from a molecular density function having densities only at centers of atoms of the given molecule and wherein each atom in the molecular density function is assigned a mass of one to determine the centroid.

23. The system of claim 20, wherein the computer-readable code is further configured to determine a magnitude of the displacement.

24. The system of claim 23, wherein the computer-readable code is further configured to:

compare a magnitude of a displacement of one of the molecules with a magnitude of a displacement of another of the molecules.

25. A system for determining three-dimensional moments of molecular property fields, the system comprising:

a memory that stores computer-readable code; and a processor operatively coupled to the memory, the processor configured to implement the computer-readable code, for a given molecule within a series of molecules;

store in the memory first data representing a shape of the given molecule at points in a first coordinate system;

store in the memory second data representing a spatial distribution of a property of the given molecule in the first coordinate system;

determine a centroid of the molecule;

determine a first second-rank tensor that defines second order moments of the spatial distribution of the property about the centroid, wherein each value of the property is assigned a value of one; and map the spatial distribution of the property of the given molecule onto a set of principal geometric axes determined by using the first second-rank tensor.

26. The system of claim 25, wherein the set comprises one principal geometric axis.

27. The system of claim 25, wherein the set comprises three principal geometric axes.

28. The system of claim 25, wherein the computer-readable code is further configured, when mapping the spatial distribution, to:

diagonalize the first second-rank tensor;

determine, from diagonalizing the first second-rank tensor, a new coordinate frame; and use the new coordinate frame to map the spatial distribution of the property of the given molecule onto the set of principal geometric axes determined by the new coordinate frame.

29. An article of manufacture comprising:

a computer readable medium having computer readable code means embodied thereon, the computer readable program code means comprising:

for a given molecule within a series of molecules:

a step to store in the memory first data representing a shape of the given molecule at points in a first coordinate system;

a step to store in the memory second data representing a spatial distribution of a property of the given molecule in the first coordinate system;

a step to determine a centroid of the given molecule based upon the first data;

a step to identify a property center in the first coordinate system wherein a first order moment of the spatial distribution of the property represented by the second data is zero; and a step to determine a displacement between the centroid and the property center.

30. The article of claim 29, wherein the first data is derived from a continuous molecular density function that describes the given molecule and wherein each atom in the molecular density function is assigned a mass of one to determine the centroid.

31. The article of claim 29, wherein the first data is derived from a molecular density function having densities only at centers of atoms of the given molecule and wherein each atom in the molecular density function is assigned a mass of one to determine the centroid.

32. The article of claim 29, wherein the computer readable program code means further comprises a step to determine a magnitude of the displacement.

33. The article of claim 32, wherein the computer readable program code means further comprises a step to compare a magnitude of a displacement of one of the molecules with a magnitude of a displacement of another of the molecules.

34. An article of manufacture comprising:
   a computer readable medium having computer readable code means embodied thereon, the computer readable program code means comprising:
      for a given molecule within a series of molecules;
         a step to store in the memory first data representing a shape of the given molecule at points in a first coordinate system;
         a step to store in the memory second data representing a spatial distribution of a property of the given molecule in the first coordinate system;
         a step to determine a centroid of the molecule;
         a step to determine a first second-rank tensor that defines second order moments of the spatial distribution of the property about the centroid, wherein each value of the property is assigned a value of one; and
         a step to map the spatial distribution of the property of the given molecule onto a set of principal geometric axes determined by using the first second-rank tensor.

35. The article of claim 34, wherein the set comprises one principal geometric axis.

36. The article of claim 34, wherein the set comprises three principal geometric axes.

37. The article of claim 34, wherein computer readable program code means further comprises, when mapping the spatial distribution:
   a step to diagonalize the first second-rank tensor;
   a step to determine, from diagonalizing the first second-rank tensor, a new coordinate frame; and
   a step to use the new coordinate frame to map the spatial distribution of the property of the given molecule onto the set of principal geometric axes determined by the new coordinate frame.

* * * * *

UNITED STATES PATENT AND TRADEMARK OFFICE
CERTIFICATE OF CORRECTION

PATENT NO. : 6,671,626 B2
DATED : December 30, 2003
INVENTOR(S) : Silverman

It is certified that error appears in the above-identified patent and that said Letters Patent is hereby corrected as shown below:

Column 8,
Line 27, before "is" and after "where" replace "1" with -- $\tilde{1}$ --.

Column 11,
Line 39, replace " $I_{xg}, I_{yg}, I_{zg}, m0, |\vec{d}|, Q_{xxc}, Q_{yyc}, Q_{zzc}, \Theta_1, \Theta_2,$ and $\Theta_3$ "

with -- $I_x^g, I_y^g, I_z^g, m0, |\vec{d}|, Q_{xx}^c, Q_{yy}^c, Q_{zz}^c, \Theta_1, \Theta_2,$ and $\Theta_3$ --.

Column 17,
Line 26, before "wherein" and after "claim", replace "14" with -- 17 --.

Signed and Sealed this

Thirteenth Day of September, 2005

JON W. DUDAS
*Director of the United States Patent and Trademark Office*